(12) United States Patent
Grünschläger et al.

(10) Patent No.: US 8,551,024 B2
(45) Date of Patent: Oct. 8, 2013

(54) METHOD AND DEVICE FOR DETERMINING A CHARACTERISTIC PROPERTY OF AN ANATOMICAL STRUCTURE

(75) Inventors: Frank Grünschläger, Feldkirchen (DE); Martin Adamski, München (DE); Andreas Oschinski, München (DE)

(73) Assignee: Brainlab AG, Feldkirchen (DE)

( * ) Notice: Subject to any disclaimer, the term of this patent is extended or adjusted under 35 U.S.C. 154(b) by 486 days.

(21) Appl. No.: 12/699,980

(22) Filed: Feb. 4, 2010

(65) Prior Publication Data

US 2010/0198110 A1    Aug. 5, 2010

Related U.S. Application Data

(60) Provisional application No. 61/167,976, filed on Apr. 9, 2009.

(30) Foreign Application Priority Data

Feb. 4, 2009    (EP) ..................................... 09152035

(51) Int. Cl.
*A61B 5/00*    (2006.01)

(52) U.S. Cl.
USPC ...................................................... 600/587

(58) Field of Classification Search
USPC ................................................ 600/587, 595
See application file for complete search history.

(56) References Cited

U.S. PATENT DOCUMENTS

| | | | | |
|---|---|---|---|---|
| 7,822,588 B2* | 10/2010 | Mueller et al. | ..................... | 703/6 |
| 2004/0230199 A1* | 11/2004 | Jansen et al. | .................... | 606/91 |
| 2006/0293614 A1* | 12/2006 | Radinsky et al. | ............. | 600/587 |
| 2008/0108912 A1* | 5/2008 | Node-Langlois | ............. | 600/587 |

OTHER PUBLICATIONS

European Search Report for corresponding Application No. 09 15 2035 dated Jun. 26, 2009.
Citak et al.; "Navigated Femoral Anteversion Measurements: A New Intraoperative Technique"; Feb. 12, 2008.
Yeon Soo Lee et al.; "3D Femoral Neck Anteversion Measurements Based on the Posterior Femoral Plane in ORTHODOC(R) System"; Sep. 29, 2006.
Prasad Sirikonda Siva et al.; "Femoral Anteversion in Infants: A Method Using Ultrasound"; Aug. 2003.
Mahaisavariya B et al.; "Morphological Study of the Proximal Femur: A New Method of Geometrical Assessment Using 3-Dimensional Reverse Engineering"; Nov. 1, 2002.
Scheys L et al.; "Personalized MR-Based Musculoskeletal Models Compared to Rescaled Generic Models in the Present of Increased Femoral Anteversion: Effect on Hip Moment Arm Lengths"; Oct. 1, 2008.

* cited by examiner

*Primary Examiner* — Max Hindenburg
(74) *Attorney, Agent, or Firm* — Renner, Otto, Boisselle & Sklar, LLP

(57) ABSTRACT

A method for determining a characteristic property of an anatomical structure from scan data which represents the position of scan points on the surface of the anatomical structure, wherein a spatial region is defined, the scan points which lie in the spatial region are determined, and the scan points which are determined to be lying in the spatial region are used to determine the characteristic property.

13 Claims, 4 Drawing Sheets

METHOD AND DEVICE FOR DETERMINING A CHARACTERISTIC PROPERTY OF AN ANATOMICAL STRUCTURE

RELATED APPLICATION DATA

This application claims the priority of U.S. Provisional Application No. 61/167,976, filed on Apr. 9, 2009, which is hereby incorporated in its entirety by reference.

FIELD OF THE INVENTION

The present invention relates to a method and device for determining a characteristic property of an anatomical structure, in particular a bone, from the position of scan points on the surface of the anatomical structure.

BACKGROUND OF THE INVENTION

In the field of medicine, it is often necessary to know a characteristic property of an anatomical structure. This is in particular a geometric property, for example the position of an axis or plane and/or the position of an axis or plane relative to another axis or plane, wherein the anatomical structure is for example a bone.

The geometric property in particular describes the relative position of "shape representatives" of the anatomical structure. The shape representatives represent a characteristic aspect of the shape of the anatomical structure. Examples of shape representatives are straight lines, planes or geometric figures. Geometric figures can be one-dimensional such as for example axes or circular arcs, two-dimensional such as for example polygons and circles, or three-dimensional such as for example cuboids, cylinders and spheres. Shape representatives can also represent parts of an anatomical structure, for example portions of a bone. The relative position between the shape representatives can be described in reference systems, for example by coordinates or vectors, or can be described by geometric variables such as for example length, angle, area, volume and ratios. The characteristic aspects which are represented by the shape representatives are for example symmetry properties which are represented for example by an axis of symmetry. Another characteristic aspect is for example the direction of extension of the anatomical structure which is for example represented by a longitudinal axis. Another characteristic aspect is for example the cross-sectional shape of an anatomical structure which is for example represented by an ellipse. Another characteristic aspect is for example the surface shape of a part of the structure which is for example represented by a plane or a hemisphere. The characteristic aspect represents in particular an abstraction of the actual shape or an abstraction of a property of the actual shape (such as for example the symmetry property or longitudinal extension).

In the case of a femoral bone, the characteristic property is for example the angle of the femoral neck axis in relation to the axis of the femoral shaft. If the anatomical structure is a spine or part of a spine, then a characteristic property is for example the kyphosis or lordosis angle between two vertebrae. The characteristic property can also be the position of the anatomical structure, for example in relation to another anatomical structure.

Various methods are known for determining a characteristic property from the position of scan data which represents scan points on the surface of the anatomical structure. To this end, a model of the anatomical structure is for example adapted to the scan data, and the property is derived from the adapted model, for example from the position of landmarks of the adapted model relative to each other. Another option is to ascertain an axis and/or plane, as an equalization axis and/or equalization plane, from the scan data and to derive the characteristic property from this.

SUMMARY OF THE INVENTION

It is the object of the present invention to provide a method and a corresponding device, to enable the characteristic property of an anatomical structure to be determined to an increased level of accuracy.

This object is solved in accordance with the invention by determining the characteristic property of the anatomical structure by defining a spatial region, determining the scan points which lie in the spatial region, and using the scan points which are determined to be lying in the spatial region to determine the characteristic property. Preferably, scan points which lie in the spatial region are predominantly or exclusively used for determining the characteristic property. If scan points which lie in the spatial region are predominantly used, this means that for example at least 70%, in particular at least 90%, 95% or 99% of the scan points lie in the defined spatial region. The defined spatial region is preferably smaller than the anatomical structure. This means that the anatomical structure does not completely lie in the defined spatial region. The defined spatial region preferably covers only a part of the surface of the anatomical structure.

The method in accordance with the invention is in particular a data processing method. The data processing method is preferably performed using technical means, in particular a computer. The computer in particular comprises a processor and in particular a memory in order to process the data, in particular electronically. The calculating steps described are in particular performed by a computer. Steps of defining for example regions and/or values are in particular steps of defining data within the framework of the technical data processing method, in particular within the framework of a program. Modifying steps in particular represent modifying the data by means of the computer. Ascertaining steps in particular comprise retrieving values which are provided at an interface of the computer and have been generated using technical means, such as for example a scanning device. These values are in particular converted by the interface into data which can be processed by the computer.

The aforementioned scan data is preferably provided to the method in accordance with the invention. Where data, regions, ranges or images are "provided", this means that they are ready for use by the method in accordance with the invention. The data, regions, ranges or images can achieve this state of being "provided" by for example being detected or captured (for example by analysis apparatuses) or by being input (for example via interfaces). The data can also have this state by being stored in a memory (for example a ROM, CD and/or hard drive) and thus ready for use within the framework of the method in accordance with the invention.

The defined spatial region is for example a (geometric) body which is delimited over a planar area and/or a curved area, for example a polyhedron such as a cuboid or a cylinder. Alternatively or additionally, the spatial region is delimited by at least one delimiting area, in particular a delimiting plane or a curved delimiting area (for example, a hemisphere). The spatial region is for example delimited by at least two delimiting areas, in particular two delimiting planes, which are preferably parallel to each other. The defined spatial region is then for example the spatial region between the delimiting areas, in particular the delimiting planes, or the region on the side of the delimiting area, in particular delimiting plane, which respectively faces away from the other delimiting area, in particular delimiting plane, i.e. the region outside the delimiting areas and/or planes.

In one embodiment of the invention, the defined spatial region is determined on the basis of landmark data which represents landmarks of the anatomical structure, i.e. which in particular define the boundaries of the spatial region. A landmark is a defined characteristic point of an anatomical structure, which is always identical or recurs with a high degree of similarity in the same anatomical structures of multiple patients. Typical landmarks are for example the epicondyles of a femoral bone or the tips of the transverse processes and/or dorsal process of a vertebra.

A model of the anatomical structure is for example adapted to the landmark data, and the defined spatial region is calculated from the adapted model. The adapting and/or calculating steps are in particular performed automatically by means of a processor. The model is for example a generic model of the anatomical structure which consists of a multitude of points. These points define the surface of the model of the anatomical structure. The points of the model, in particular their two-dimensional or three-dimensional location, are preferably represented by model data.

When adapting the model to the landmark data—so-called matching or morphing—the generic model is altered, for example scaled or distorted, such that the landmarks in the landmark data match corresponding landmarks of the model.

The model is thus matched as far as possible to the actual anatomical structure. This is achieved for example by altering the locations of the points of the model, i.e. in particular by altering the model data. The landmark data preferably represents the positions of exactly three landmarks.

The landmark data, which is provided to the method as input data, can be ascertained directly or indirectly. If directly ascertained, the corresponding landmark is directly scanned; if indirectly ascertained, two or more points are scanned, and the landmark is calculated from these points.

After the characteristic property has been calculated, the defined spatial region is optionally altered and the characteristic property recalculated. This is in particular advantageous when the plausibility of the characteristic property can be ascertained or when a measure of the accuracy of the calculation is determined when the characteristic property is calculated.

In one specific application, the anatomical structure is a femoral bone and the characteristic property is the angle of the femoral neck axis. The angle of the femoral neck axis is the angle between the neck and the shaft of the femoral bone. In this application, the landmark data represents for example a lateral mid-neck point, the mid-point of the head of the femoral neck and the mid-point of the epicondylar axis of the femoral bone. These three points define a plane which is referred to as the coronary plane or femoral plane. Both the neck axis and the shaft axis of the femoral bone lie in this plane.

The lateral mid-neck point is a point in the middle of the femoral neck in the lateral region, for example the mid-point of the region in which the piriformis abuts the femoral bone. In order to determine the mid-point of the head of the femoral neck, a multitude of scan values, for example 150, on the surface of the head of the femoral neck are measured, and an equalization sphere is positioned using the measured scan points, in particular by means of a processor. The mid-point of the equalization sphere is defined as the mid-point of the head of the femoral neck. The mid-point of the epicondylar axis corresponds to the mid-point of the connecting straight line between the lateral and medial epicondylar point.

The invention also relates to a device for determining a characteristic property of an anatomical structure, comprising: a computer which is designed to perform the method described above, in the form of the individual method steps; and a scanning device for ascertaining scan points on the surface of the anatomical structure, in order to generate the scan data and/or landmark data which is supplied to the computer for processing. The scanning device is for example a pointer which is provided with a marker device, in particular a reference star. The position, i.e. the location and the alignment, of the pointer and therefore the location of the tip of the pointer can be determined via the marker device and/or reference star. To this end, the marker device and/or reference star is for example detected by means of a 3D camera. A marker device can be a reference star, a pointer and/or one or more markers.

The function of a marker is to be detected by a marker detection device (for example, a camera or an ultrasound receiver), such that its spatial position (i.e. location and/or alignment) can be ascertained. Such markers can be active markers. An active marker emits for example electromagnetic radiation and/or waves, wherein said radiation can be in the infrared, visible and/or ultraviolet spectral range. The marker can however also be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A "reference star" refers to a device with a plurality of markers, advantageously three markers, attached to it, wherein the markers are attached to the reference star such that they are stationary and advantageously detachable, such that a known (and advantageously fixed) position of the markers relative to each other is created. The position of the markers relative to each other can be individually different for each reference star being used within the framework of a surgical navigation method, in order to enable a surgical navigation system to identify the corresponding reference star on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of markers to an object (for example, a bone or a medical instrument) in order to be able to detect the spatial position of the object (i.e. its location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to. Where it is clear from the context, the term "reference star" can also refer to a reference star with at least one marker attached to it. Such a system consisting of a reference star and at least one marker can also be called a marker star.

The invention also relates to a computer program which, when it is executed or loaded on a computer, causes the computer to perform the method steps of the method described above.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments. The computer and/or data processing device can in particular represent a guidance information device which includes means for outputting guidance information. The guidance information can be output, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element and/or vibration element incorporated into an instrument).

It is possible to combine individual features or all the features of the described embodiments with each other or to omit features which are not essential to the invention from combinations of features.

BRIEF DESCRIPTION OF THE DRAWINGS

The present invention shall be explained in more detail on the basis of an example embodiment.

DETAILED DESCRIPTION

Figure 1:
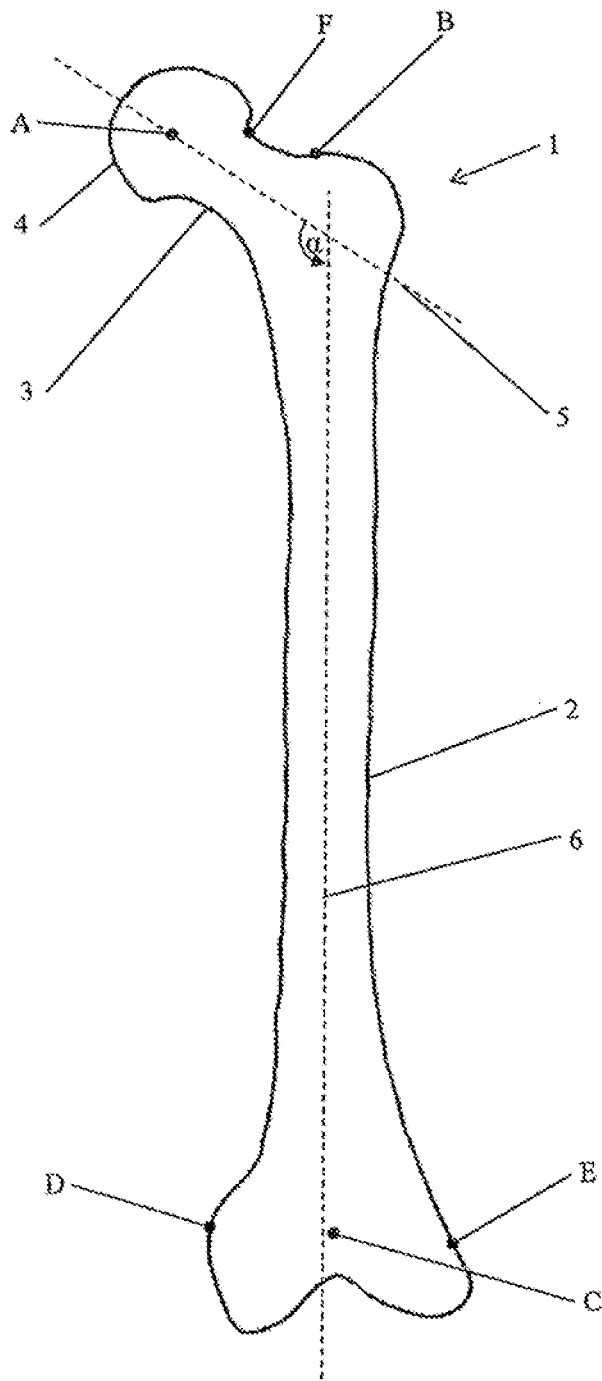
FIG. 1 shows a schematic representation of a femoral bone.

FIG. 1 schematically shows a femoral bone 1 comprising a shaft 2, a neck 3 and a head 4. A characteristic property of the bone 1 is the femoral neck angle $\alpha$ between the femoral neck axis 5 and the shaft axis 6.

In order to calculate the femoral neck angle $\alpha$, landmark data is first generated by measuring three landmarks. The first landmark is the mid-point A of the head 4 of the femoral neck. In order to determine the point A, a multitude of scan points on the head of the femoral neck are recorded. The number of scan points recorded is for example between 100 and 200, in particular about 150. The mid-point A of the head 4 of the femoral neck is calculated from the scan points recorded, for example as the mid-point of an equalization sphere with respect to the scan points.

The second landmark is represented by the lateral mid-neck point B. This is a point in the middle of the femoral neck 3 in the lateral region, for example the mid-point of the area in which the piriformis abuts the femoral bone 1.

The third landmark is the mid-point C of the epicondylar axis. The mid-point C of the epicondylar axis is the mid-point of the connecting straight line between the medial epicondylar point D and the lateral epicondylar point E. In order to calculate the mid-point C, the two epicondylar points D and E are scanned and the mid-point between them is calculated.

The three landmarks A, B and C serve as the basis for defining a spatial region. Scan points which lie in this defined spatial region are exclusively taken into account in a subsequent method step of determining the angle $\alpha$ of the femoral neck axis 5. Alternatively, scan points which lie in this defined spatial region are predominantly taken into account. This means that for example at least 70%, at least 90%, at least 95% or at least 99% of the scan points taken into account lie within the defined spatial region. This alternative also applies to all the other embodiments.

In order to define said spatial region, the coronary plane—also referred to as the femoral plane—of the femoral bone 1 is first determined from the landmark data. The coronary plane is the plane in which the landmarks A, B and C lie. A generic model of a femoral bone is then adapted such that the landmarks A, B and C represented by the landmark data corresponds to the landmarks of the model. To this end, the model is aligned such that the femoral neck axis and the shaft axis of the model lie in the coronary plane. The model is then scaled and/or distorted such that the mid-point A of the head of the femoral neck and the mid-point C of the epicondylar axis match the corresponding points of the model. Aligning, scaling or distorting the model means altering the model data.

Since the adapted model does not necessarily correspond completely to the shape of the actual femoral bone 1, the angle of the model femoral neck axis does not usually correspond exactly to the actual angle $\alpha$ of the femoral neck axis 5. The model femoral neck axis, which is provided with the reference sign 7 in FIGS. 2 and 3, does however serve as a starting point for defining the spatial region. The model femoral neck axis is the femoral neck axis 7 of the generic model.

In the present example embodiment, the defined spatial region is limited by two parallel planes which are each perpendicular to the model femoral neck axis 7. Only the scan points of the surface of the femoral bone 1 which lie between these two parallel planes 8 and 9 are taken into account when calculating the angle $\alpha$ of the femoral neck axis 5. The planes are in particular represented by plane data which preferably comprises a point in the plane and a vector which is normal to the plane.

Figure 2:
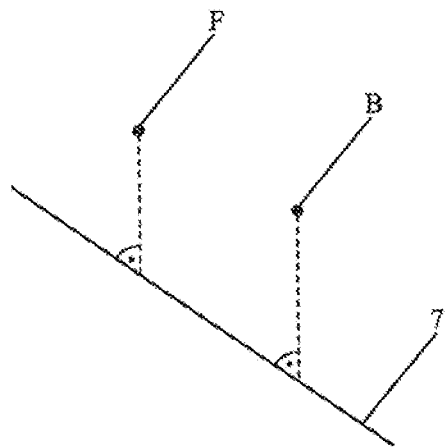
FIG. 2 shows a model femoral neck axis, together with two scan points.

Determining the two delimiting planes 8 and 9 is shown in FIG. 2. The first delimiting plane 8 is the delimiting plane which is perpendicular to the model femoral neck axis 7 and in which the lateral mid-neck point B lies. In order to determine the second delimiting plane 9, a head-neck junction point F is used which marks the transition from the femoral neck 3 to the femoral head 4 and is for example likewise scanned. The delimiting plane 9 is positioned such that it contains the point F.

Before the characteristic property of the anatomical structure is calculated, i.e. before the angle of the femoral neck axis is calculated, the delimiting planes 8 and 9 are optionally shifted along their surface normals relative to each other, such that their distance is altered. The original distance is for example increased or decreased by an absolute distance, for example 1 mm, 2 mm, 5 mm or 1 cm, or multiplied by a factor, for example 0.75, 0.8, 0.9, 1.1, 1.2 or 1.25. Preferably, both delimiting planes are shifted by the same distance relative to their original location.

Figure 3:
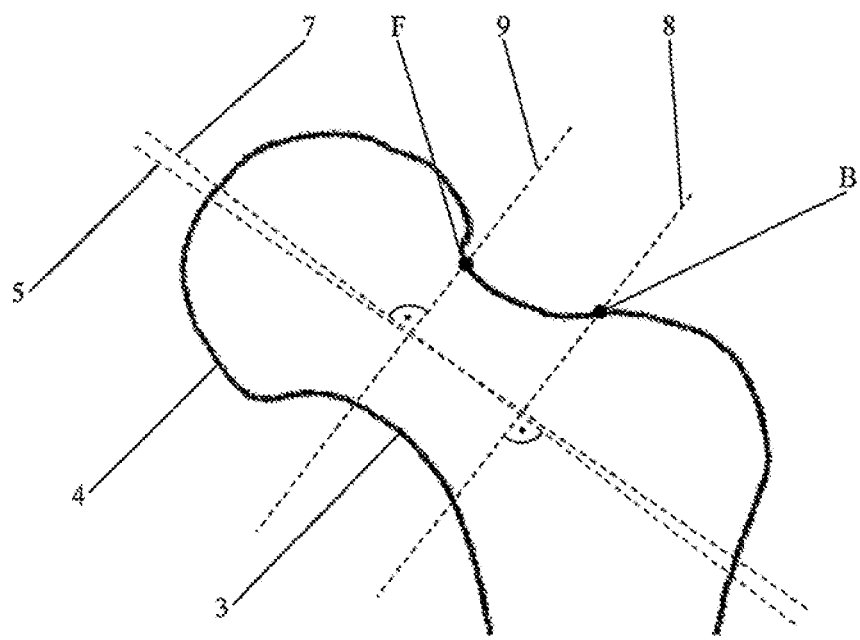
FIG. 3 shows a part of the femoral bone, together with two delimiting planes.

FIG. 3 shows a detail of the femoral bone 1 together with the actual femoral neck axis 5, the model femoral neck axis 7 and the two delimiting planes 8 and 9. The delimiting planes 8 and 9 each form a right angle with the model femoral neck axis 7. Scan points of the surface of the femoral bone 1 which do not lie between the two delimiting planes 8 and 9 are not taken into account when calculating the angle α of the femoral neck axis 5.

The defined spatial region can optionally be limited further, for example limited to a cuboid or cylindrical region. In the case of a cuboid region, two opposite faces of a cuboid lie in the delimiting planes 8 and 9. A second pair of opposite faces of a cuboid lie for example parallel to the coronary plane; the third pair of opposite faces of a cuboid are for example perpendicular to the coronary plane. The distance between the faces of a cuboid which form the second and third pair, respectively, is preferably defined between 4 cm and 7 cm, or is selected in accordance with the distance between the delimiting planes 8 and 9, for example as 0.5, 0.75, 1, 1.25 or 1.5 times this distance.

In the case of a cylindrical spatial region, the end faces of the cylinder lie in the delimiting planes 8 and 9, and the axis of the cylinder corresponds to the model femoral neck axis 7. The radius of the cylinder is either an absolute value, for example 2 cm, 3 cm or 4 cm, or a relative value, for example 0.1, 0.2, 0.25, 0.5, 1, 1.25, 1.5 or 2 times the distance between the two delimiting planes 8 and 9.

Figure 4A:
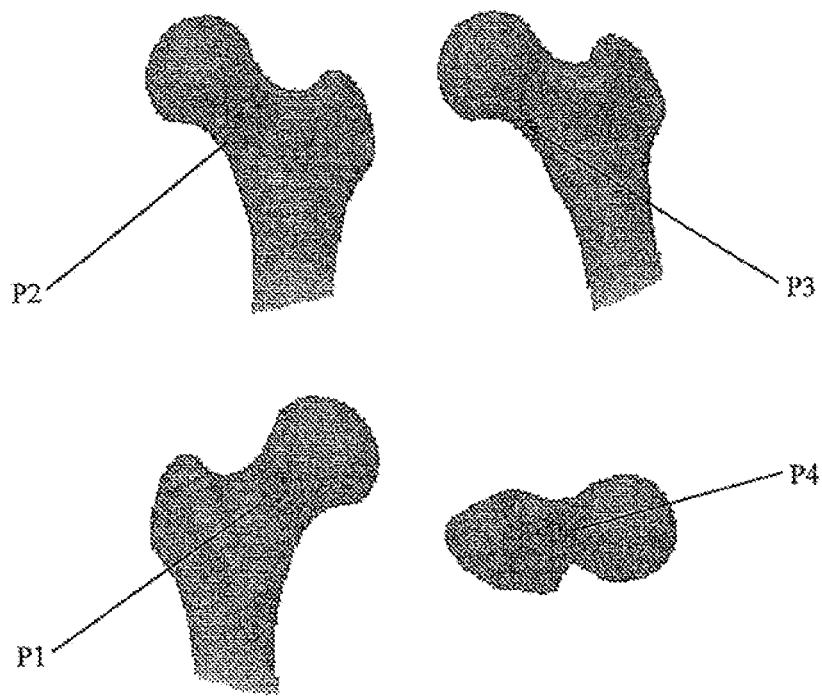
FIGS. 4a and 4b show scan points for determining the femoral neck axis.

Determining the position of the femoral neck axis 5 is explained on the basis of FIG. 4. FIG. 4a shows four sets of scan points on the posterior, superior, anterior and inferior side of the femoral neck 3. These four sets of points are referred to in FIG. 4a by P1, P2, P3 and P4. They each lie in the spatial region defined and/or delimited as described above.

Figure 4B:
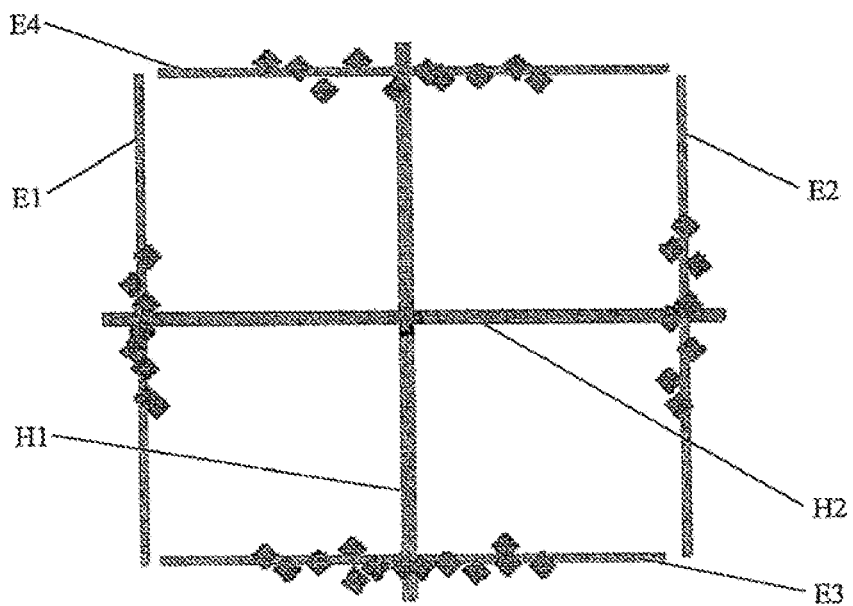

FIG. 4b shows the four sets of points P1, P2, P3 and P4 from a lateral view which runs exactly or approximately in the direction of the femoral neck axis. An equalization plane is positioned using each of the sets of points, for example such that the sum of the distances or the sum of the squared distances between all the scan points in the respective set of points and the equalization plane is minimized. The equalization planes are provided with the reference signs E1, E2, E3 and E4, wherein the equalization plane E1 belongs to the set of points P1, and so on.

In another step, two auxiliary planes H1 and H2 are calculated. The auxiliary plane H1 lies centrally between the posterior equalization plane E1 and the anterior equalization plane E2; the auxiliary plane H2 lies centrally between the inferior equalization plane E3 and the superior equalization plane E4. In the case of parallel planes, a central position between two planes means that the auxiliary plane lies parallel to the two planes and exhibits the same distance from both planes; in the case of non-parallel planes, a central position between two planes means that the auxiliary plane represents the angle bisector between the two planes. The femoral neck axis 5 is then the intersecting straight line between the first auxiliary plane H1 and the second auxiliary plane H2.

Figure 5:
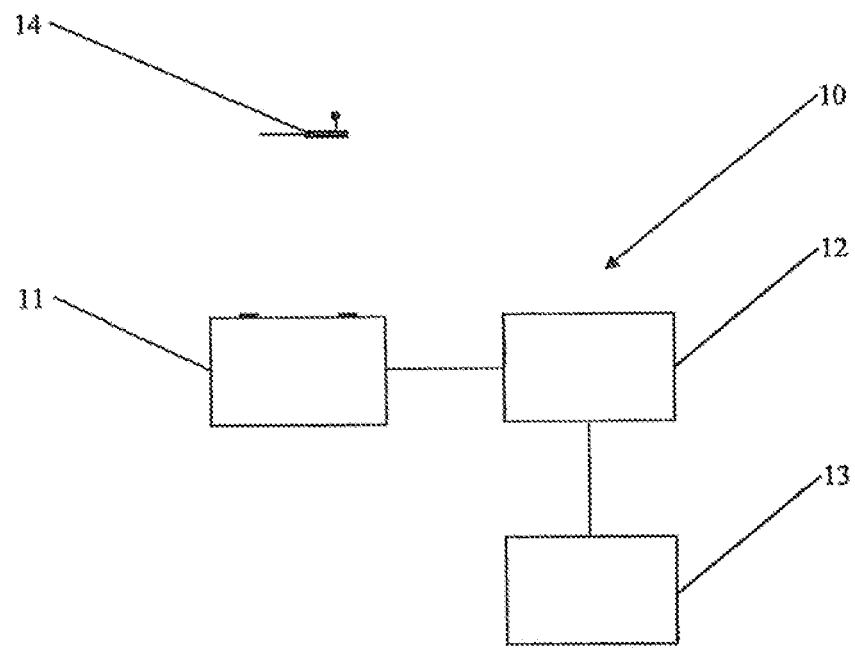
FIG. 5 shows a device for determining a characteristic property of an anatomical structure.

FIG. 5 schematically shows a device 10 for determining a characteristic property of an anatomical structure. The device 10 comprises a 3D camera 11, a computer 12 and an indicating device 13. The 3D camera 11 is designed to ascertain the position, i.e. the location and spatial alignment, of a pointer 14. The pointer 14 comprises a tip which can be brought into contact with a point to be scanned. The pointer 14 also comprises a marker device, which is only symbolically shown, in the form of a reference star.

The 3D camera 11 comprises two object lenses which are merely indicated in FIG. 5 and by means of which a stereoscopic image of the pointer 14 and the marker device situated on it is recorded. The position of the pointer 14, in particular its tip, can be calculated from the stereoscopic image and the location of the 3D camera 11, for example in the 3D camera 11 or in the computer 12 connected to the 3D camera 11.

The computer 12 is designed and programmed to perform the method steps for determining a characteristic property of an anatomical structure. To this end, information such as the characteristics of the pointer 14 or the characteristics of the generic model of the anatomical structure are stored.

An indicating device 13 is connected to the computer 12. The computer 12 can communicate with an operator of the device 10 via the indicating device 13 and an inputting device (not shown). The next landmark to be scanned is for example displayed on the indicating device 13, for example highlighted in a representation of the generic model of the anatomical structure. Alternatively or additionally, the characteristic property of the anatomical structure and/or guidance information is displayed on the indicating device 13. One possible form of guidance information indicates that the point which the tip of the pointer 14 is situated at is situated outside the defined spatial region. Another possible form of guidance information is that enough measurement data for determining the characteristic property of the anatomical structure has been recorded.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for determining a characteristic property of an anatomical structure, comprising:
    obtaining scan data that represents a position of a plurality of scan points on a surface of the anatomical structure;
    defining a spatial region relative to the anatomical structure, wherein at least part of the anatomical structure lies outside the defined spatial region, the defined spatial region delimited by at least two planes, wherein the at least two planes do not intersect within the anatomical structure;
    determining which scan points of the plurality of scan points are within the defined spatial region; and
    determining the characteristic property of the anatomical structure based on the scan points that are within the spatial region.

2. The method according to claim 1, wherein the anatomical structure is a bone.

3. The method according to claim 1, wherein defining the spatial region includes defining the spatial region as a geometric body which is delimited over at least one of a planar area or a curved area.

4. The method according to claim 1, wherein defining the spatial region includes determining the spatial region from landmark data which represents landmarks of the anatomical structure.

5. The method according to claim 4, wherein determining the spatial region includes adapting a model of the anatomical structure to the landmark data, and calculating the defined spatial region from the adapted model.

6. The method according to claim 4, wherein determining the spatial region from landmark data includes using landmark data that represents the position of three landmarks.

7. The method according to claim 1, further comprising after the characteristic property has been calculated, altering the defined spatial region and recalculating the characteristic property.

8. The method according to claim 1, wherein the anatomical structure is a femoral bone, and the characteristic property is the angle of the femoral neck axis.

9. The method according to claim 8, wherein the landmarks represented by the landmark data is a lateral mid-neck point, the mid-point of the head of the femoral neck and the mid-point of the epicondylar axis of the femoral bone.

10. A device for determining a characteristic property of an anatomical structure from scan data which represents a position of scan points on a surface of the anatomical structure, comprising:
    a computer configured to
        i) determine the scan points which are within a defined spatial region, the defined spatial region delimited by at least two planes that do not intersect within the anatomical structure, and
        ii) determine the characteristic property based on the scan points determined to be within the defined spatial region; and
    a scanning device for ascertaining scan points on the surface of the anatomical structure, in order to generate at least one of the scan data or landmark data which is supplied to the computer for processing.

11. The device according to claim 10, wherein the device is configured to determine ate characteristic of an anatomical structure comprising a bone.

12. A non-transitory computer readable medium comprising computer executable instructions adapted to perform the method steps of a method according to claim 1.

13. The method according to claim 1, wherein defining the spatial region comprises:
    defining a first plane that intersects the anatomical structure;
    defining a second plane that intersects the anatomical structure, the second plane spaced apart from the first plane; and
    defining the spatial region to be a region between the first and second planes.

* * * * *